(12) United States Patent
Rappin

(10) Patent No.: US 6,245,558 B1
(45) Date of Patent: Jun. 12, 2001

(54) TRANSFER LOOP

(75) Inventor: Craig A. Rappin, Buffalo Grove, IL (US)

(73) Assignee: Virotek, L.L.C., Buffalo Grove, IL (US)

( * ) Notice: Subject to any disclaimer, the term of this patent is extended or adjusted under 35 U.S.C. 154(b) by 0 days.

(21) Appl. No.: 09/437,524

(22) Filed: Nov. 10, 1999

(51) Int. Cl.[7] .................................................. C12M 1/26
(52) U.S. Cl. .................. 435/309.3; 435/30; 422/100; 73/864.72
(58) Field of Search .................... 435/309.3, 30; 422/100; 436/180; 73/864.72

(56) References Cited

U.S. PATENT DOCUMENTS 3,875,015 * 4/1975 Wadley et al. .................... 435/309.3

* cited by examiner

Primary Examiner—David A. Redding
(74) Attorney, Agent, or Firm—Wood, Phillips, VanSanten, Clark & Mortimer

(57) ABSTRACT

A transfer loop has a loop, a stem, and an optional main body member. The loop is connected to the stem and encloses a slit resulting in a discontinuous loop. The slit is positioned either to one side of the loop or at the bottom of the loop and aligned relative to the long central axis of the transfer loop. The transfer loop is adapted to pick up an aliquot of fluid from a first surface and to release the aliquot of fluid downward onto a second surface. Specifically, the aliquot of fluid is directed through the slit and deposited in a non-random manner onto the second surface. More specifically, pressure does not have to be applied to the stem to cause the loop to flatten against the second surface in order to facilitate release of the aliquot of fluid.

15 Claims, 11 Drawing Sheets

TRANSFER LOOP

FIELD OF THE INVENTION

This invention relates to a transfer loop carrying a fluid drop and, more particularly, to a transfer loop including a slit.

BACKGROUND OF THE INVENTION

This invention relates to the transfer of a small amount of liquid medium from a first position to a second position. Particularly, the invention relates to the transfer of a fluid droplet from a sample source to a surface. More specifically, the invention relates to a transfer loop that can release a fluid a droplet onto a surface in a non-random manner.

Over the years the fields of clinical biochemical analysis, microbiological analysis, virological analysis, forensic and chemical analysis in general have seen a massive surge in diagnostic and chemical assay methods that enable fast and rapid analysis of numerous parameters. Concomitant with this rapid pace of development has been the parallel development of small sample analysis wherein qualitative analysis and in some cases precise quantitative analysis may be performed on a fluid droplet or aliquot of fluid. For example, a pregnancy test kit and a HIV qualitative test kit require only a small sample to detect the presence of biological markers that indicate a pregnancy or a HIV infection, respectively.

There has also been a growing demand for rapid testing. For example, the physician or physician's assistant might collect a blood or urine sample and immediately analyze the sample in the doctor's surgery without need to transfer the sample to a central laboratory for independent analysis. The patient gets their test result quickly and the physician has more control over the whole process. There has been an explosive growth in demand for home test kits such as personal pregnancy test kits. Likewise, diabetics have benefited from the development of small test kits that can measure blood glucose levels based on the analysis of a single droplet of blood. Home patients, for example kidney dialysis patients, benefit from the ease with which bodily fluid samples such as blood and urine might be tested using a home test kit. Home test kits often involve handling an aliquot of fluid. Thus there is a demand for a simple way of transferring an aliquot of fluid from a sample site to the test kit.

Out in the field, technicians, industrial chemists, field biologists, industrial microbiologists, and engineers sometimes need to test various systems without having to waste time trekking samples back to the laboratory for analysis. For example, a water biologist or chemist might need to check for the presence of a specific pesticide in a river or stream that feeds a fresh water reservoir. Testing for a particular bacterium such as *E. coli* in seawater alongside tourist beaches might also be of interest to an environmentalist. The field scientist, technician, physician, nurse, environmental activist, Environmental Protection Agency ("EPA") Inspector, field engineer, home patient, or research student might take a sample in the form of an aliquot of fluid and deposit the aliquot of fluid on a test surface for analysis.

The conditions for field scientists and field engineers are frequently not ideal. Cold and damp hands might make transferring aliquots of fluid or fluid droplets from a sample source to a test surface difficult and haphazard. Likewise the physician or physician's assistant is sometimes under pressure and needs a simple means to transfer, for example, an aliquot of blood from a bleed site to a test surface. Further, the advent of home test kits and their use by largely unskilled adults increases the chances of mishap in transferring an aliquot of fluid, such as a droplet of blood from a lanced finger or a droplet of urine, to a test surface for analysis. Thus there is a need for a simple transfer device that transfers an aliquot of fluid from a sample site to a test surface.

A Pasteur pipette might be used to transfer a small droplet of fluid from the sample source to a test surface. For example, a Pasteur pipette might be used to transfer an aliquot of blood from a bleed site on a lanced finger to a test surface. However, the basic operation of the Pasteur pipette relies on a pumping action wherein an elastic rubber or plastic teat is pressed between the thumb and index finger to create a partial vacuum. The blood droplet may then be sucked into the mouth of the Pasteur pipette and thence into the stem of the pipette by slowly releasing the teat. The droplet is then dispensed onto the test surface by a controlled squirting action upon pressing the teat between the index finger and thumb. Even with expert use of finger and thumb it is possible to generate a small aerosol spray of blood leading to an accidental inhalation risk. The contact surface might include a well into which the pipette could be inserted prior to expulsion of the blood droplet. While the use of a well would decrease the likelihood of accidental inhalation of blood mist, the physician or physician's assistant may still accidentally release at least part of the aliquot of blood from the pipette prior to successfully inserting the mouth of the pipette into the well. The Pasteur pipette is a potential health hazard when it is in unskilled hands. Specifically, anyone in close proximity to an inexpertly used Pasteur pipette is presented with an inhalation risk.

The blood droplet may be transferred from the surface of the finger to the test surface by means of a static transfer device such as a glass rod. However, there is a risk of the blood droplet falling from the rod and causing blood splatter on impact with the floor or other surface. This presents a safety hazard to the physician, nurse or other medical professional. Alternatively the blood droplet may be transferred from the finger by directly smearing the finger onto the test surface. This might be undesirable because the test surface might contain test reagents that should not come into direct contact with the skin of a patient.

A loop may be used to transfer a fluid droplet such as a droplet of blood. Various transfer loops, including bacteriological transfer loops, are described in the literature. For example, U.S. Pat. No. 4,010,077 describes an improved bacteriological transfer loop for use in bacteriological identification. However, such loops of the prior art require a streaking action in order to effect transfer.

U. S. Pat. No. 3,147,197 describes a bacteriological transfer loop for transferring liquid medium from one culture medium to another. Such transfer loops of the prior art are frequently problematic when used to transfer an aliquot of fluid from a sample source to a specific location on a surface. To initiate the release of the fluid droplet, the loop might have to be angled or flattened against the surface. This often causes a problem because the aliquot of fluid appears to have a mind of its own and will sometimes not transfer from the loop to a specific location on a surface. Flattening the loop against the surface may cause damage to a sensitive test surface when the test surface comprises a matrix that is sensitive to pressure or excessive contact with a loop. Thus there is a need for a transfer loop that does not require much effort on the part of the operator to cause the release of a fluid droplet onto a surface. In addition, aligning or flattening the loop relative to the surface can lead to undesirable consequences wherein the fluid droplet is transferred in a somewhat random manner onto a surface. Using a well with walls that define a small radius might help to ensure that the fluid droplet is placed where it is needed. However, the deeper the well the less the operator can bend or flex the loop relative to the surface because the stem of the loop will contact the sides of the well. Also, it is hard to see if the droplet has in fact been deposited onto the surface. Hence there is a need for a transfer loop that can release a fluid droplet onto a surface in a non-random manner.

BRIEF SUMMARY OF THE INVENTION

Accordingly, an object of this invention is to provide a transfer loop capable of carrying and releasing a fluid droplet in a non-random manner onto a surface.

Another object is to provide a transfer loop that does not have to be pressed or aligned against a surface in order to facilitate the release of an aliquot of fluid.

The transfer loop of the invention includes a discontinuous loop, a slit, a stem, and an optional main body member. The discontinuous loop is attached to the stem. The stem is attached to an optional main body at the opposite end from the discontinuous loop. The discontinuous loop encloses the slit, which may be positioned at various points around the loop. The transfer loop is adapted to pick up an aliquot of fluid and to release the aliquot of fluid downward onto a surface. Specifically, the aliquot of fluid is directed through the slit and deposited in a non-random manner onto the surface. More specifically, pressure does not have to be applied to the stem to cause the loop to flatten against the surface in order to facilitate release of the aliquot of fluid.

BRIEF DESCRIPTION OF THE DRAWINGS

The following is a brief description of the drawings that are presented for the purposes of illustrating the invention and not for purposes of limiting the same.

DETAILED DESCRIPTION OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims.

Figure 1:
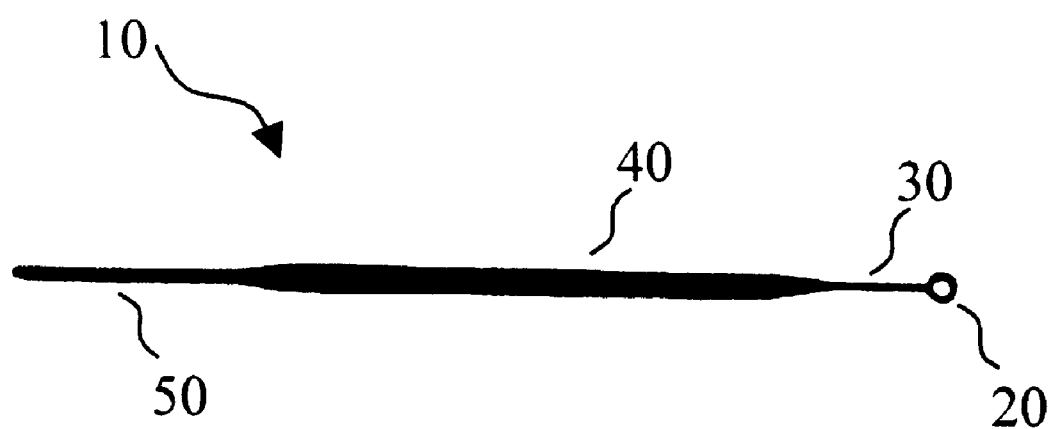
FIG. 1 illustrates a transfer loop of the prior art.

Referring to FIG. 1, which depicts a transfer loop 10 known in the prior art, a loop 20 is attached to a stem 30. A main body 40 is attached to the distal end of the stem 30 relative to the loop 20. The main body 40 includes a tapered end 50.

Operators of the transfer loop 10 of the prior art typically found that in order to deposit the fluid droplet onto a surface, the loop 20 had to be laid flat or juxtapositioned at awkward angles against the surface to facilitate the release of the fluid droplet onto the surface. In addition to wasting time, juxtapositioning the loop 20 often led to an undesirable result wherein the aliquot of fluid was not deposited at the desired location. If the loop 20 was used to deposit an aliquot of fluid onto a flat surface at the bottom of a well, the walls of the well often interfered with the juxtapositioning of the loop 20.

Figure 2:
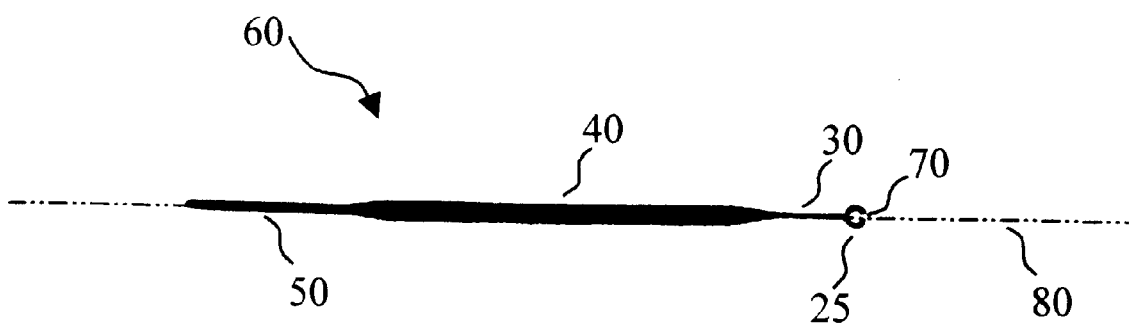
FIG. 2 illustrates a transfer loop according to one embodiment of the invention.

FIG. 2 shows a transfer loop 60 according to one aspect of the invention. A discontinuous loop 25 includes a slit 70. The loop 20 is attached to a stem 30 at a point furthest away from the slit 70. A main body 40 is attached to the distal end of stem 30 relative to the discontinuous loop 25. The main body 40 includes a tapered end 50. The slit 70 is aligned with the long central axis 80 of the main body 40.

Figure 3:
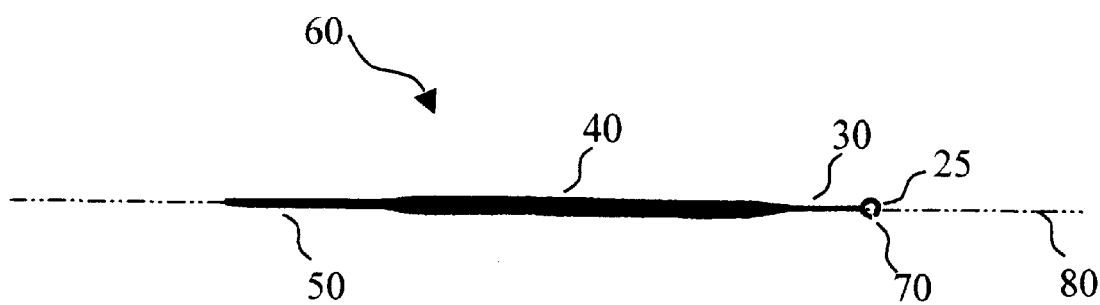
FIG. 3 illustrates a transfer loop according to one embodiment of the invention.

FIG. 3 shows a transfer loop 60 according to another aspect of the invention. The discontinuous loop 25 includes a slit 70. The discontinuous loop 25 is attached to the stem 30. A main body 40 is attached to the distal end of the stem 30 relative to the discontinuous loop 25. The main body 40 includes the tapered end 50. The slit 70 is not aligned with the long central axis 80 of the main body 40.

Figure 4:
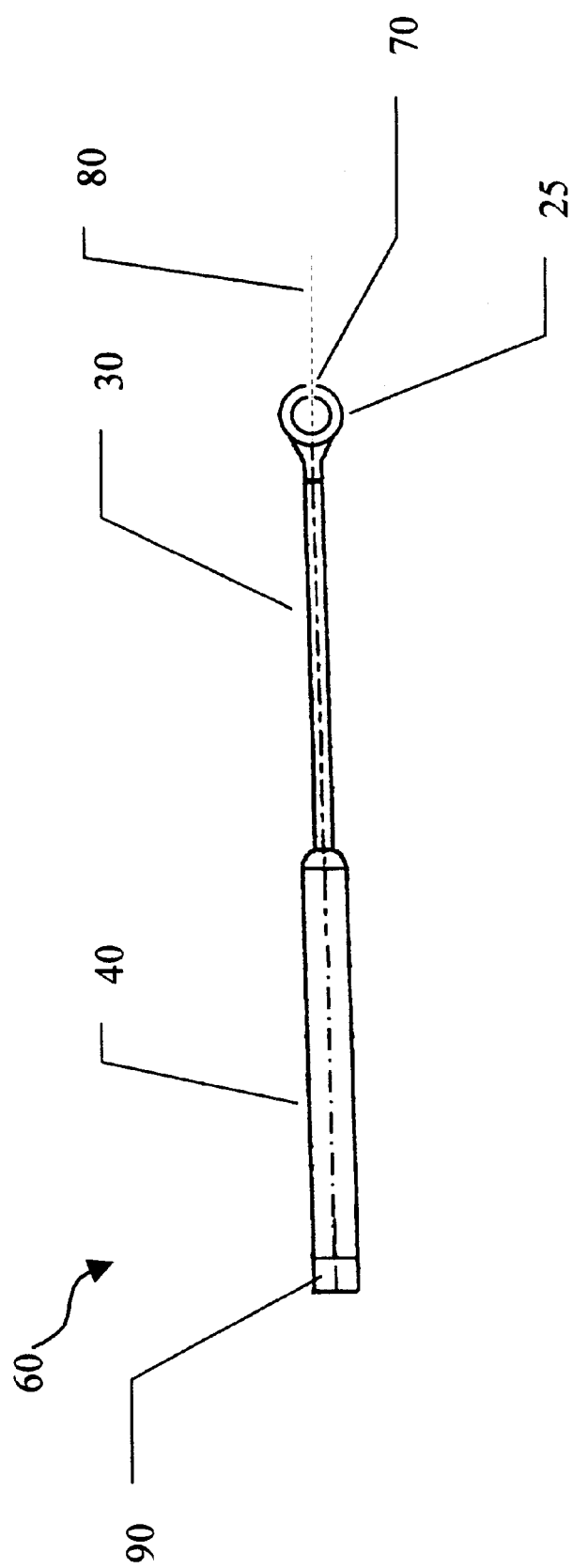
FIG. 4 illustrates a transfer loop according to one aspect of the invention.
Figure 5:
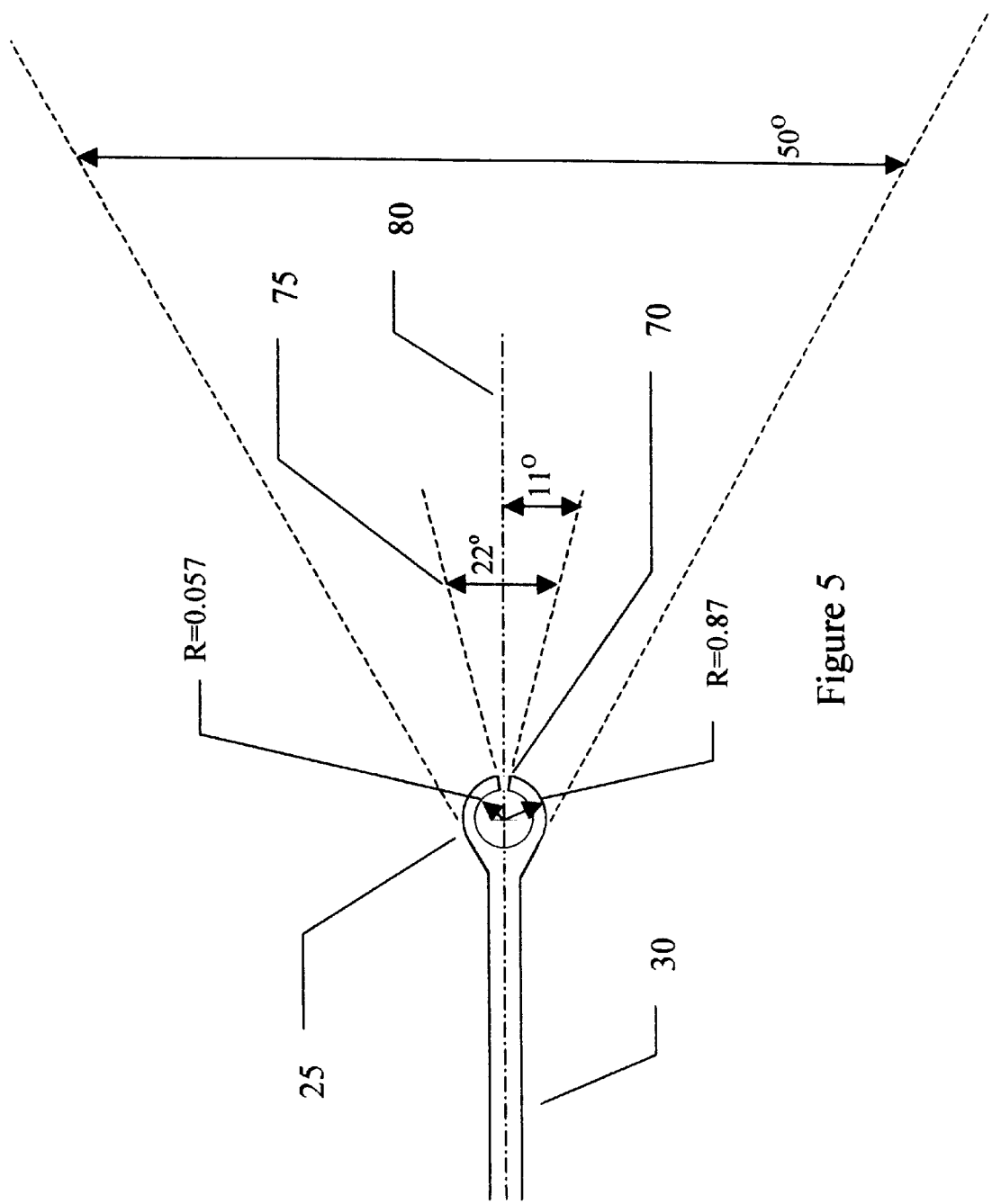
FIG. 5 illustrates a transfer loop according to one aspect of the invention.

Referring to FIG. 4, which shows a transfer loop 60 according to a preferred aspect of the invention, the transfer loop 60 is a single piece of molded plastic. The discontinuous loop 25 defines the slit 70. The discontinuous loop 25 is attached to a stem 30 at a point furthest away from the slit 70. The stem 30 is attached to a main body 40. The main body 40 includes a block end 90. The slit 70 of FIG. 4 is shown enlarged in FIG. 5. The slit 70 defines an angle 75 of about 22° about the central axis 80. The angle 75 will hereafter be referred to as the "slit separation angle 75".

It should be understood that the length of the stem 30 and the handle 40 are not critical and may vary. It should also be understood that the handle 40, though desirable, is optional. The stem 30 might be extended and take the place of the handle 40.

Figure 6:
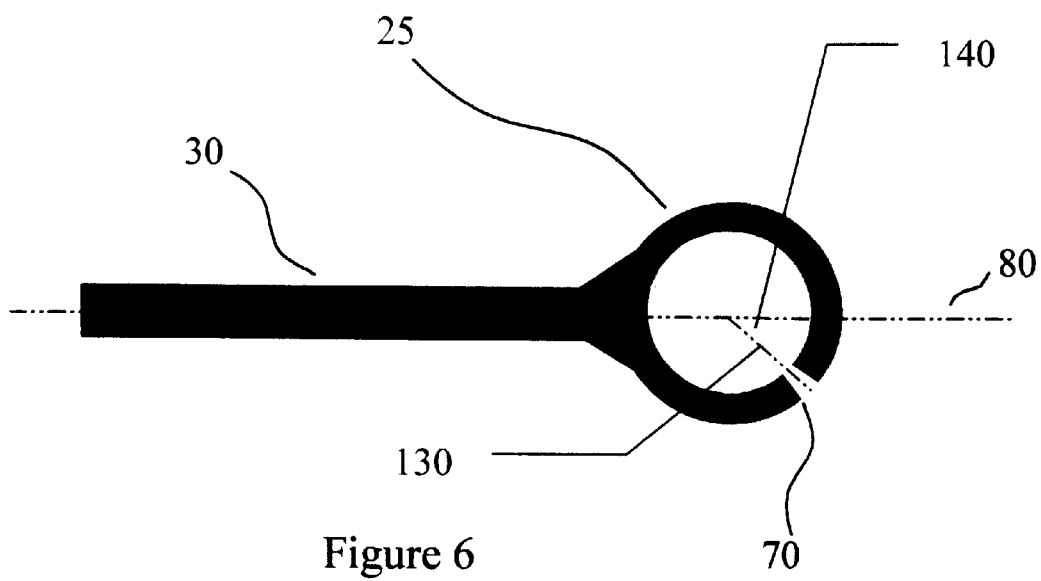
FIG. 6 illustrates a transfer loop according to one aspect of the invention.

Referring to FIG. 6, which shows the discontinuous loop 25 connected to stem 30, the slit 70 is to one side of the central long axes 80. In this aspect of the invention, the slit 70 is not directly opposite the connection between the stem 30 and the discontinuous loop 25. A reference axis 130, which extends from the center of the discontinuous loop 25 and intersects the mid-point of slit 70, produces an angle 140. The angle 140 will hereafter be referred to as the "slit angle 140". In this embodiment of the invention, the slit angle 140 is about 30°.

It should be understood that the slit angle 140 might vary between about 0° and 90°. More preferably, the slit angle 140 is any value between about 0° and 45°. Still more preferably the slit angle 140 is in the range between about 0° and 30°. It should be further understood that the slit 70 is directly opposite the stem 30 when the slit angle 140 is about 0° (see FIGS. 2, 4, 5, and 7).

The transfer loop 60 of the present invention is adapted to pick up an aliquot of fluid from a sample source and to release the aliquot of fluid in a non-random manner onto a test surface. The terms "aliquot of fluid" and "fluid droplet" shall hereafter be regarded as equivalent terms. Specifically, the aliquot of fluid is directed downward through the slit 70 and deposited in a non-random manner onto a test surface. More specifically, side directed pressure does not have to be applied to the stem 30 to cause the loop 25 to flatten against the test surface in order to facilitate release of the aliquot of fluid onto a surface. The terms "surface" and "test surface" shall hereafter be regarded as equivalent terms.

It should be understood that the sample source might be a bleed site such as a lanced finger, wherein the aliquot of fluid collected by the transfer loop 60 is an aliquot of blood. It should be further understood that the sample source might be non-human in origin, for example a pet cat, a dog, a farm animal, a wild animal, a microbial culture broth, and an insect colony. It should be further understood that the sample source might share both inanimate and living characteristics such as cutting oil used to cool and lubricate cutting bits in machine lathes. Cutting oil is an oil emulsion that is usually recycled continuously from lathe to lathe around a factory shop floor. The cutting oil is open to the air and frequently contaminated with colonies of bacteria and unwanted chemicals or chemical derivatives resulting from concomitant bio-deterioration due to the presence of bacteria that use the cutting oil as a carbon source. Infected cutting oils can present a serious aerosol spray hazard and lead to an infection in a worker who works in close proximity to a lathe. Thus, cutting oils require some monitoring and aliquots of cutting oil may be taken using the transfer loop 60 of the invention and transferred to a test surface designed to assess at least one parameter of special interest such as the presence of bacteria or the presence of an oil break down product.

It should be further understood that the sample source might be substantially inanimate in nature such as the interior of a cooling tower, a chemical storage vat, and a NASA interplanetary space probe and landing vehicle.

It should be understood that the term "non-random manner" describes the manner in which the discontinuous loop 25 of the invention is able to deposit a fluid droplet at a desired location on a surface. The surface is preferably an absorbent surface. Hence the discontinuous loop 25 of the invention is distinguished over the transfer loop 10 of the prior art because the discontinuous loop 25 is designed to deposit an aliquot of fluid, in a non-random manner, onto a surface.

It should be understood that the improvement in transfer loop technology is provided by the slit 70 that directs the deposit of the fluid droplet onto a surface. Specifically, the fluid droplet is directed from the discontinuous loop 25 via the slit 70 and deposited onto a surface without requiring a person to flex the loop against the second surface. It should be understood that the transfer loops of the prior art often required the user to press or flatten the loop against the second surface in order to hasten the transfer of the fluid droplet from the loop 20 to the second surface. The flattening of the loop 20 against the second surface would often deform the loop 20 or stress the connection between the loop 20 and the stem 30.

In a preferred mode of use, the fluid droplet is released on contacting the discontinuous loop 25 with an absorbent surface. The fluid droplet is released from the discontinuous loop 25, via the slit 70, and is immediately absorbed by the absorbent surface.

The transfer loop 60 may also be used to collect an aliquot of fluid from sample sources that include, but are not limited to: a water supply system, a sewage system, a water-oil boundary in a ship fuel tank, a stream, a river, a recent snow fall, a commercial or domestic water tank, and a chemical spill. Other sample sources include, but are not limited to: a lanced boil on the surface of a patient's skin, a bleed site, a urine specimen, an oozing Eustachian tube, an oozing lesion, a specimen of saliva, a specimen of mucous, an eye droplet, a specimen of hair lotion, a leaf puddle, a specimen of condensed steam distillate, and an organic solvent. Once the aliquot of fluid is collected by the transfer loop 60, the aliquot of fluid is transferred to a test surface wherein the aliquot of fluid is deposited onto the test surface in a non-random manner via the slit 70.

Figure 7:
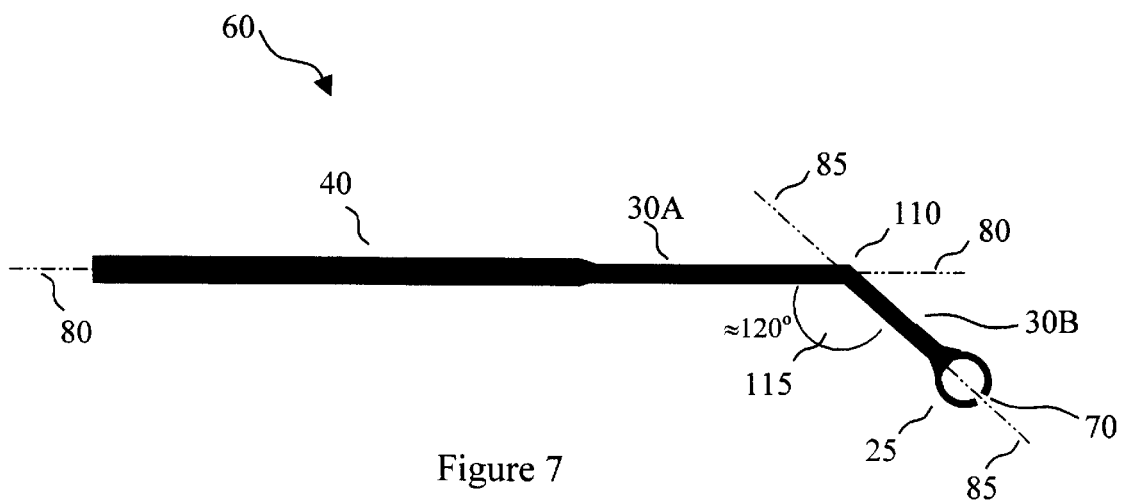
FIG. 7 illustrates a transfer loop according to one aspect of the invention.

Referring to FIG. 7, which shows a transfer loop 60 according to one embodiment of the invention, the stem 30 is separated into two components 30A and 30B due to a bend 110. The bend 110 encloses an angle 115 of about 120°. The slit 70 is aligned with the central axis 85 of stem component 30B. In this configuration, the transfer loop 60 might be used to collect an aliquot of fluid from a difficult-to-access sample site. The terms "sample site" and "sample source" will hereafter be regarded as equivalent terms.

The internal angle 115 is in the range between about 90° and 180°. The length of the stem 30B between the bend 110 and the discontinuous loop 25 is not critical. However, the length of the stem 30B should be sufficient to cope with the height of a well 100 (see FIGS. 10 and 11). Specifically, the length of the stem 30B should not interfere with depositing a fluid aliquot onto a test surface enclosed by the well 100.

It should be understood that when the internal angle 115 is equal to 180°, the stem components 30A and 30B would be aligned with the axes 80. When the internal angel 115 is 0°, the stem components 30A and 30B would merge to result in the single stem 30.

Figure 8:
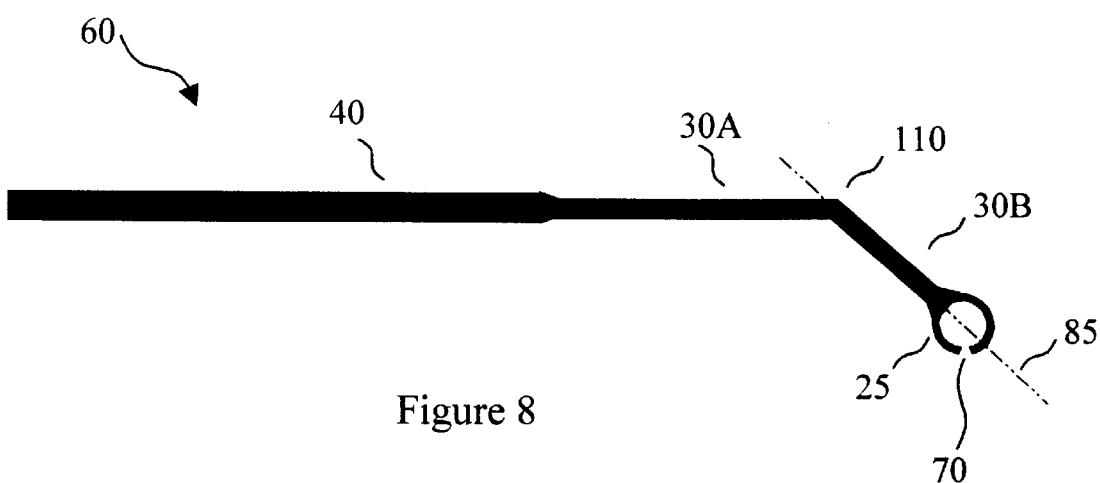
FIG. 8 illustrates a transfer loop according to one aspect of the invention.
Figure 9:
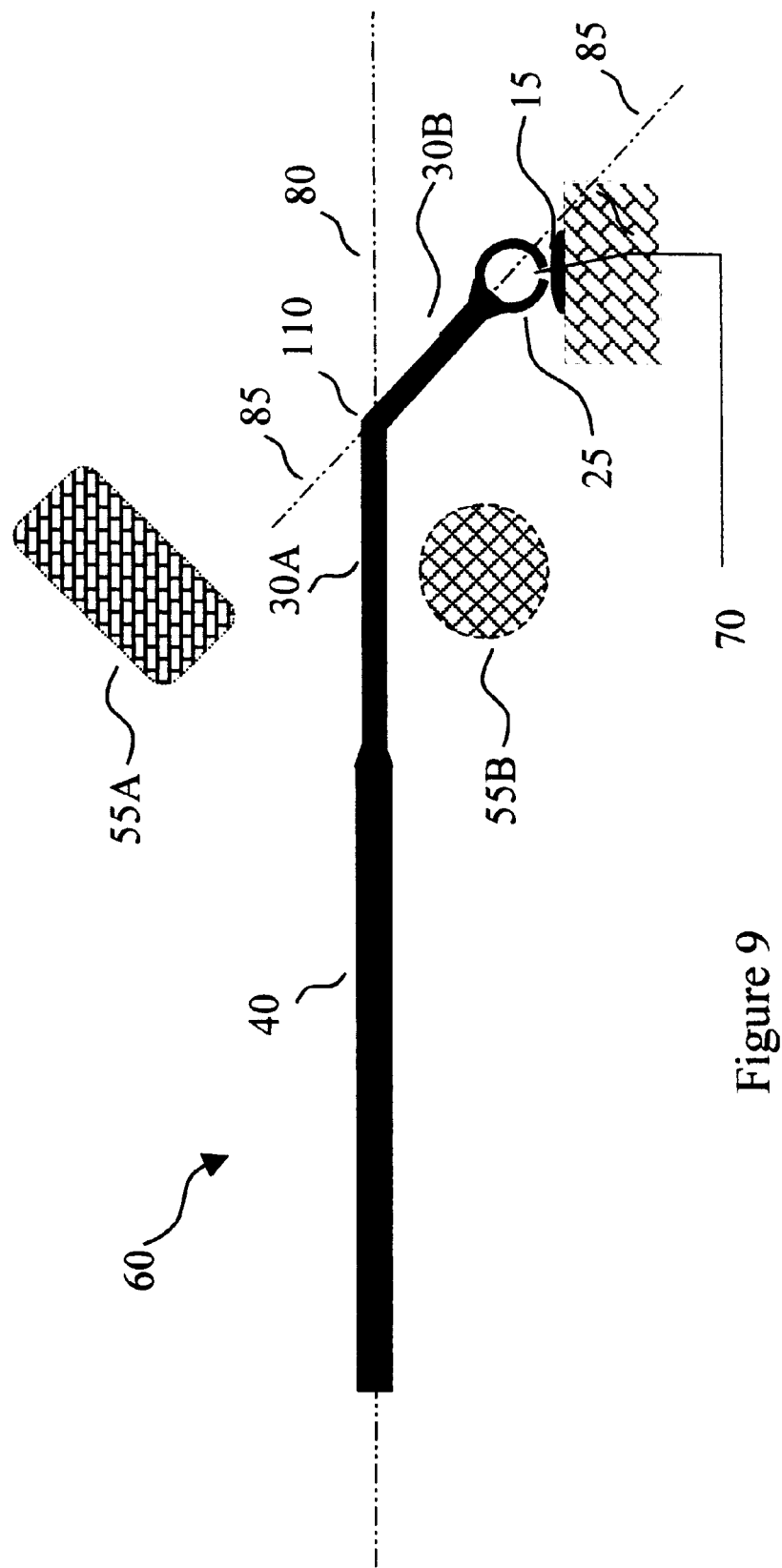
FIG. 9 is a schematic showing how a transfer loop, according to one aspect of the invention, might be used to collect an aliquot of fluid from an inaccessible sample source.

Referring to FIG. 8 and FIG. 9, which show a transfer loop 60 according to one embodiment of the invention, the slit 70 is not aligned with the central axis 85 of stem component 30B. In this embodiment the transfer loop 60 might be used to obtain an aliquot of fluid from a rather inaccessible sample 15 located behind an obstruction 55 (see FIG. 9). The sample 15 might be located inside a machine, a water-cooling tower, a commercial kitchen appliance, an empty industrial fermentor, or a recently washed cream dispenser in a cream cake factory. The operator might locate the slit 70 over the sample 15 by following a few simple steps listed below:

(i) Positioning the main body 40 in the horizontal plane with the stem 30 (i.e. stem components 30A and 30B) facing in the direction of sample 15;
(ii) Rotating the main body 40 until the axes 80 and 85 coincide in the horizontal plane;
(iii) Approximately positioning the discontinuous loop 25 above the sample 15 all the while keeping the axes 80 and 85 in the horizontal plane; and
(iv) Rotating the main body 40 until the discontinuous loop 25 is located approximately above the sample site 15.

(v) Collecting an aliquot of fluid from the sample site 15. The operator might rotate the main body 40, and hence the transfer loop 60, by holding the main body 40 between the index finger and thumb and then simultaneously moving the thumb and finger in opposite directions in a plane roughly perpendicular to the axis 80.

Figure 10:
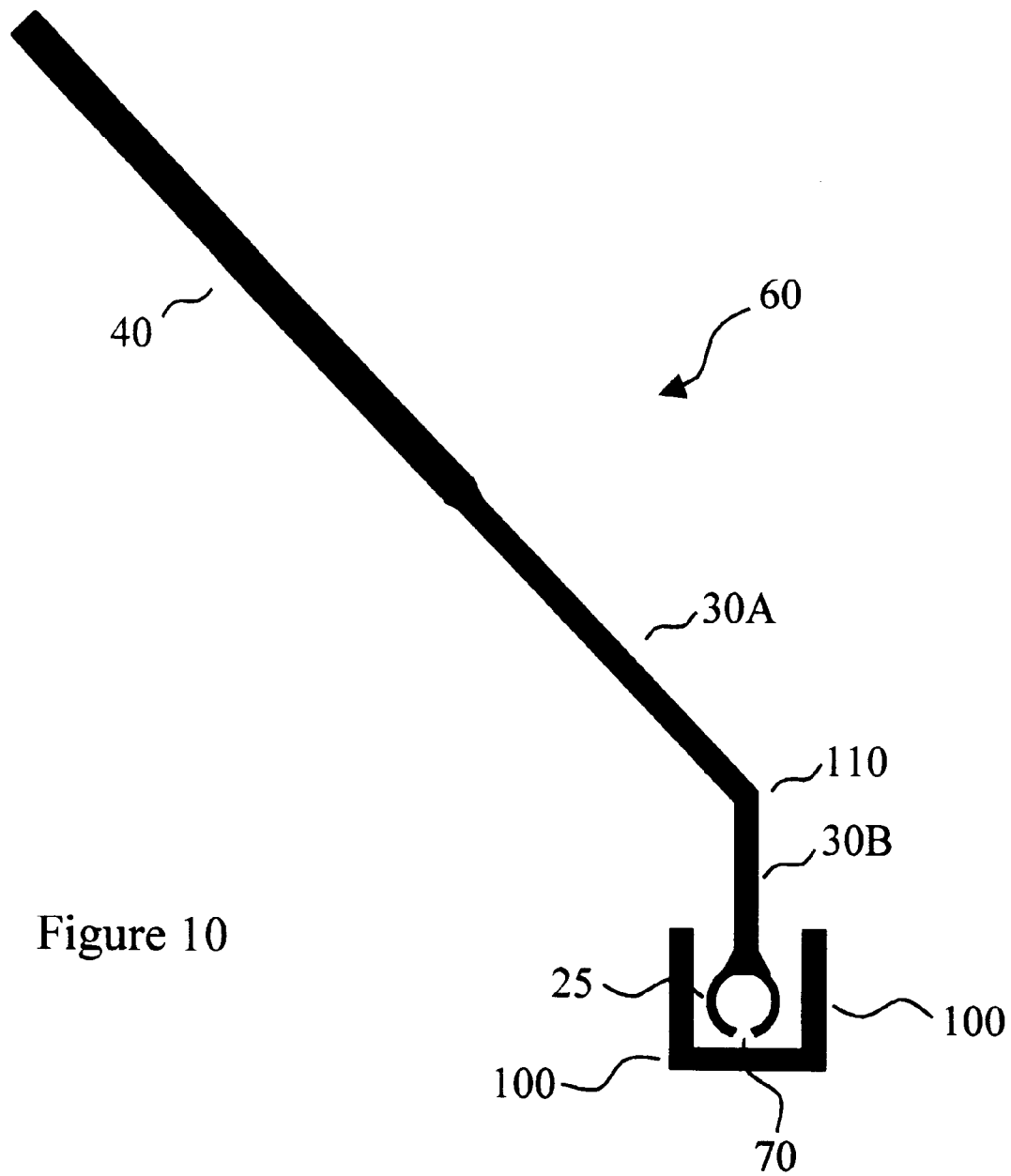
FIG. 10 illustrates a transfer loop according to one aspect of the invention.

Referring to FIG. 10, which shows a transfer loop 60 according to one embodiment of the invention, the discontinuous loop 25 is located within the confines of a well 100 (shown in cross-section). During normal use of the transfer loop 60, the length of the stem component 30B should be sufficient to avoid stem component 30A colliding or interfering with the walls of the well 100. In this embodiment, the transfer loop 60 is configured to deposit an aliquot of fluid onto a test surface on the bottom of the well 100, the well 100 having substantially vertical walls.

Figure 11:
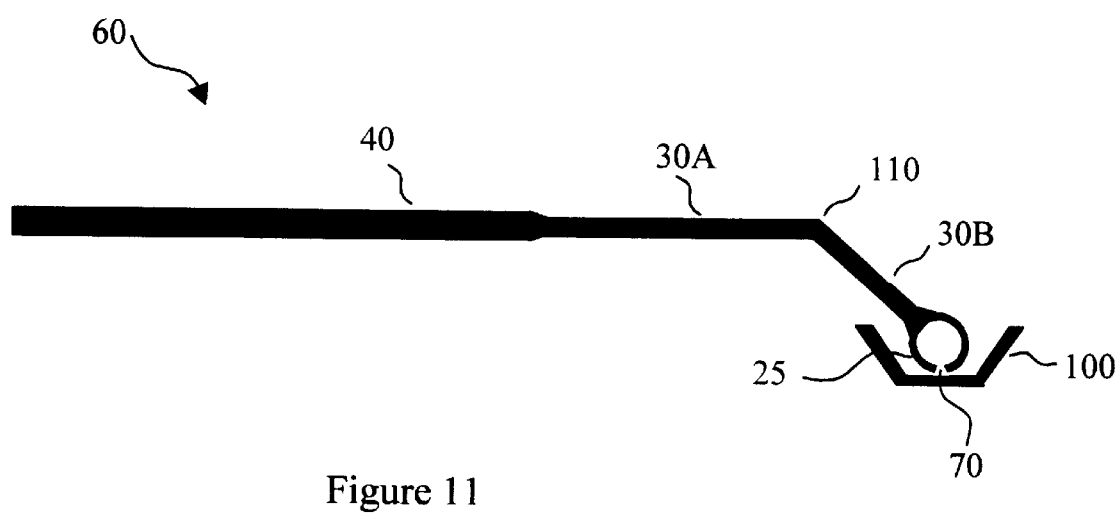
FIG. 11 illustrates a transfer loop according to one aspect of the invention.

Referring to FIG. 11, which shows a transfer loop 60 according to one embodiment of the invention, the discontinuous loop 25 is located within the confines of a well 100 (shown in cross-section). The walls of the well 100 are sloping outwards in an upwards direction. During normal use of the transfer loop 60, the length of the stem component 30B should be sufficient to avoid stem component 30A colliding or interfering with the walls of the well 100. In this embodiment, the transfer loop 60 is configured to deposit an aliquot of fluid onto a test surface on the bottom of the well 100, the well 100 having walls that slope outwards in an upward direction.

While the invention is described above in connection with preferred or illustrative embodiments, these embodiments are not intended to be exhaustive or limiting of the invention. Rather, the invention is intended to cover all alternatives, modifications and equivalents included within its spirit and scope of the invention, as defined by the appended claims.

What is claimed is:

1. A transfer loop for carrying a fluid droplet and depositing the fluid droplet in a non-random manner onto a surface, the transfer loop comprises:
   a loop including a slit in said loop to define a discontinuous loop;
   a stem attached to said discontinuous loop to provide said transfer loop, said slit positioned within the loop such that said transfer loop deposits a fluid droplet in a non-random manner onto a surface without flexing or flattening said loop against said surface.

2. The transfer loop according to claim 1, wherein said transfer loop further comprises a main body attached to the distal end of said stem relative to the discontinuous loop.

3. The transfer loop according to claim 1, wherein said discontinuous loop further comprises a slit angle in the range between about 0° and 90°.

4. The transfer loop according to claim 1, wherein said discontinuous loop further comprises a slit angle in the range between about 0° and 45°.

5. The transfer loop according to claim 1, wherein said discontinuous loop further comprises a slit angle in the range between about 0° and 30°.

6. The transfer loop according to claim 1, wherein said discontinuous loop further comprises a slit angle of about 0°.

7. The transfer loop according to claim 1, wherein said discontinuous loop further comprises a slit angle of about 30°.

8. The transfer loop according to claim 1, wherein said discontinuous loop further comprises a slit separation angle of about 22°.

9. The transfer loop according to claim 1, wherein said slit in said loop is directly opposite the stem.

10. The transfer loop according to claim 1, wherein said loop is attached to said stem at a point furthest away from the slit.

11. The transfer loop according to claim 1, wherein said transfer loop further comprises a bend in said stem.

12. The transfer loop according to claim 1, wherein said bend further comprises an internal angle, said internal angle is in the range between about 90° and 180°.

13. The transfer loop according to claim 1, wherein said bend further comprises an internal angle, said internal angle is about 120°.

14. A method for transferring a fluid droplet from a first surface and non-randomly placing said fluid droplet directly onto a second surface using a transfer loop, said transfer loop comprises a loop including a slit in said loop to define a discontinuous loop, said discontinuous loop comprises a slit angle, said slit angle is in the range between about 0° and 45°, said method comprising:
   contacting said discontinuous loop with a fluid droplet on said first surface; and
   depositing said fluid droplet onto said second surface, said fluid droplet is transferred directly from said loop via said slit and deposited non-randomly onto said second surface.

15. The method according to claim 14, wherein said second surface is an absorbent surface.

* * * * *